(12) United States Patent
Kim et al.

(10) Patent No.: US 8,931,345 B2
(45) Date of Patent: Jan. 13, 2015

(54) APPARATUS FOR MEASURING CONCRETE STRENGTH AND SLIP FORM METHOD FOR CONSTRUCTING VERTICAL CONCRETE COLUMN MEMBER USING SURFACE WAVE VELOCITY MEASUREMENT DEVICE

(71) Applicants: Hee Seok Kim, Anyang-si (KR); Young Jin Kim, Goyang-si (KR); Won Jong Chin, Seoul (KR); Hye Jin Yoon, Goyang-si (KR); Byung Suk Kim, Goyang-si (KR)

(72) Inventors: Hee Seok Kim, Anyang-si (KR); Young Jin Kim, Goyang-si (KR); Won Jong Chin, Seoul (KR); Hye Jin Yoon, Goyang-si (KR); Byung Suk Kim, Goyang-si (KR)

(73) Assignee: Korea Institute of Construction Technology, Goyang-si, Gyeonggi-do (KR)

( * ) Notice: Subject to any disclaimer, the term of this patent is extended or adjusted under 35 U.S.C. 154(b) by 331 days.

(21) Appl. No.: 13/649,961

(22) Filed: Oct. 11, 2012

(65) Prior Publication Data
US 2013/0091952 A1   Apr. 18, 2013

(30) Foreign Application Priority Data

Oct. 17, 2011   (KR) ........................ 10-2011-0105945

(51) Int. Cl.
*G01N 29/00* (2006.01)
*E04C 3/34* (2006.01)
*G01N 29/07* (2006.01)

(52) U.S. Cl.
CPC *E04C 3/34* (2013.01); *G01N 29/07* (2013.01); *G01N 2291/0232* (2013.01); *G01N 2291/02827* (2013.01); *G01N 2291/0423* (2013.01); *G01N 2291/102* (2013.01)
USPC .................................. 73/632; 73/598; 73/602

(58) Field of Classification Search
USPC ..................................... 73/632, 598, 600, 602
See application file for complete search history.

(56) References Cited

U.S. PATENT DOCUMENTS

| | | | | |
|---|---|---|---|---|
| 5,369,997 A * | 12/1994 | Roberts et al. | ................... | 73/598 |
| 5,540,096 A * | 7/1996 | Woodcock et al. | ............. | 73/579 |
| 6,367,330 B1 * | 4/2002 | Schafer | ........................... | 73/598 |
| 6,672,162 B2 * | 1/2004 | Hirose | ............................ | 73/579 |
| 7,987,728 B2 * | 8/2011 | Song et al. | ...................... | 73/786 |

FOREIGN PATENT DOCUMENTS

| | | |
|---|---|---|
| JP | 2007-121123 | 5/2007 |
| JP | 2008-157775 | 7/2008 |
| JP | 2010-266378 | 11/2010 |
| KR | 10-2012-0060270 A | 6/2012 |
| KR | 10-1195500 | 10/2012 |

OTHER PUBLICATIONS

Kim, H.S. et al., "A Study on the Determination of the Slip-up Speed for Slip-Form System Using Ultrasonic Test," (with English abstract), 36th Regular Academic Conference of Korean Society of Civil Engineers, 2010, 7 pages.
Kim, H.S. et al., "A Study on the Determination of the Slip-up Speed for Slip-Form System Using Surface Wave Velocity in Concrete," (with English abstract), 2010 Spring Academic Conference Sponsored by Journal of the Korea Concrete Institute (JKCI), 4 pages.

* cited by examiner

*Primary Examiner* — J M Saint Surin
(74) *Attorney, Agent, or Firm* — Fenwick & West LLP (57) ABSTRACT

An apparatus for measuring the strength of concrete using a surface wave velocity including an ultrasonic transmission and reception probe is provided. The apparatus is configured to include a surface wave velocity measurement device including an ultrasonic transmission probe and an ultrasonic reception probe. Further, a method of constructing the slip form of a concrete column member is provided. The method is capable of reducing the construction period by raising a concrete form rapidly and safely using a method of determining the slip-up time of the slip form based on the strength of concrete measured by the apparatus.

6 Claims, 9 Drawing Sheets

APPARATUS FOR MEASURING CONCRETE STRENGTH AND SLIP FORM METHOD FOR CONSTRUCTING VERTICAL CONCRETE COLUMN MEMBER USING SURFACE WAVE VELOCITY MEASUREMENT DEVICE

CROSS REFERENCE TO RELATED APPLICATION

This application claims the benefit of Korean Patent Application No. 10-2011-0105945, filed on Oct. 17, 2011, which is incorporated by reference herein in its entirety.

BACKGROUND OF THE INVENTION

1. Field

The present invention relates to a method of constructing a vertical concrete column member, such as the pylon of a bridge and a bridge pier, using a slip form and an apparatus for measuring the strength of concrete for the method and, more particularly, to an apparatus for measuring the strength of concrete using a surface wave velocity including an ultrasonic transmission and reception probe configured to include an surface wave velocity measurement device including an ultrasonic transmission probe and an ultrasonic reception probe and to measure the propagation velocity of an surface wave propagating along concrete and measure the strength of the concrete based on the measured propagation velocity and a method of constructing the slip form of a concrete column member capable of reducing the construction period by raising a concrete form rapidly and safely in such a way as to determine the slip-up time of the slip form based on the strength of concrete measured by the apparatus for measuring the strength of concrete in performing a slip form construction method of producing a vertical concrete column member, such as the pylon of a bridge or a bridge pier, by casting concrete while stepwise raising a concrete form (i.e., a slip form) that is slid.

2. Description of the Related Art

When constructing a bridge, in particular, a concrete column member, such as the concrete pylon or concrete pier of a long bridge, the concrete is stepwise casted. That is, a concrete column member having a desired height is constructed in such a way as to cast concrete to a predetermined height, cure the cast concrete so that it has predetermined strength, and cast the concrete over the cured concrete again.

In this construction, a concrete form that slides and moves, that is, a slip form, is mainly used. In a construction method using the slip form, a concrete column member having a desired height is constructed by repeating a process of assembling the slip form, installing reinforcing bars inside of the slip form, casting concrete, curing the concrete, installing reinforcing bars on the cured concrete, raising the slip form, and placing concrete. Next, the slip form is dismantled.

In the slip form construction method of constructing a concrete column member using a slip form as described above, the setting time of concrete is very important. The term "early setting time" herein means a curing time, that is, the initial condensation reaction time of concrete that the concrete is taken to have strength that may maintain structural stability even though the concrete exists from the slip form after the concrete is cast. The early setting time is a very important factor that determines the time that the slip form is raised, that is, a "slip-up time of slip form". The entire construction period and construction efficiency depend on the slip-up time of the slip form. Accordingly, in constructing a column member using a slip form, the casting velocity of concrete and the slip-up time of the slip form can be determined only when the concrete setting time is accurately known.

The inventors of the present invention studied that the strength of concrete could be measured using the propagation velocity of an surface wave that propagates along concrete, released a thesis entitled "A Study on the Determination of the Slip-up Speed for Slip-Form System using Ultrasonic" in the 36$^{th}$ Regular Academic Conference of Korean Society of Civil Engineers that was held in 2010 as disclosed in Prior Technical Document, and also published a thesis entitled "A Study on the Determination of the Slip-up Speed for Slip-Form System Using the Speed of a surface Wave in Concrete" in the 2010 Spring Academic Conference sponsored by Journal of the Korea Concrete Institute (JKCI) that was held in November 2010.

Thereafter, the inventors of the present invention have developed an apparatus for measuring the velocity of an surface wave which has a new construction and has a construction easily installed in a slip form, in order to commercialize technology for measuring the strength of concrete using the propagation velocity of an surface wave that propagate along concrete, additionally induced a new and advanced method of constructing a slip form for a concrete column member which constructs the concrete column member by raising the slip form based on the strength of concrete measured by the apparatus for measuring the strength of an surface wave, and filed a Korean Patent Application No. 10-2010-0121211 in 2010.

SUMMARY

Accordingly, the present invention has been made keeping in mind the above problems occurring in the prior art, and an object of the present invention is to construct a concrete column member stably and rapidly by measuring the strength of concrete that is cast in a slip form quantitatively, precisely, and in such a way not to give damage to the concrete, checking the early setting time of the concrete, and determining the slip-up time of the slip form in casting and constructing the concrete column member, such as a concrete pylon or a concrete pier, stepwise according to the slip-up the slip form.

Another object of the present invention is to further improve the utilization of a method and increase accuracy when measuring the strength of concrete by measuring the velocity of an surface wave that moves along the concrete using an apparatus for measuring the propagation velocity of the surface wave having a simple structure, measuring the strength of the concrete based on the measured velocity of the surface wave, and raising a slip form based on the measured strength of the concrete.

In order to accomplish the above objects, the present invention provides an apparatus for measuring the strength of concrete, which is installed in a slip form and configured to detect ultrasonic waves propagated along concrete by radiating the ultrasonic waves to the concrete, measure the velocity of an surface wave included in the ultrasonic waves based on the detected ultrasonic waves and measure the strength of the concrete based on the measured velocity of the surface wave.

Particularly, in accordance with the present invention, there is provided an apparatus for measuring the strength of concrete, including an surface wave velocity measurement device installed in concrete and configured to generate ultrasonic waves to the concrete and to measure ultrasonic waves propagated along the concrete and a controller configured to calculate a propagation velocity $V_{Surface\ wave}$ of an surface wave included in the ultrasonic waves by converting a signal measured by the surface wave velocity measurement device and calculate the strength of the concrete based on a result of the calculation. Here, the surface wave velocity measurement device includes an ultrasonic transmission probe configured to generate the ultrasonic waves within the concrete, a first contact plate configured to have the ultrasonic transmission probe installed therein, closely adhered to a surface of the concrete, and configured to transfer the ultrasonic waves of the ultrasonic transmission probe to the concrete, an ultrasonic reception probe configured to measure the ultrasonic waves propagated along the concrete, a second contact plate configured to have the ultrasonic reception probe installed therein, closely adhered to the surface of the concrete, and configured to transfer the ultrasonic waves from the concrete to the ultrasonic reception probe, and a frame configured to have two openings formed therein at an interval, configured to have the first contact plate and the second contact plate inserted into and combined with the respective openings, and assembled into a slip form.

In the apparatus for measuring the strength of concrete, the bottom of the first contact plate and the bottom of the second contact plate may be disposed in such a way as to be more protruded than the bottom of the frame; coupling pieces may be installed in the first contact plate and the second contact plate, respectively; an elastic spring member may be disposed between a member fixed to the frame and the top surface of each of the coupling pieces; and when the bottom of each of the first contact plate and the second contact plate more protruded than the bottom of the frame comes in contact with the surface of the concrete and thus retreats in an upward direction of the frame, the coupling piece may move and thus the elastic spring member may generate elastic force, and the elastic force of the elastic spring member functions as pressure that pushes each of the first contact plate and the second contact plate in a downward direction thereof.

In this case, the member fixed to the frame may include a pillar member vertically installed in the frame and a locking member provided at a top of the pillar member; the pillar member may penetrate the coupling piece; and the elastic spring member may be included between a top of the coupling piece and the locking member in the pillar member after the pillar member penetrates the coupling piece, and thus when the coupling piece moves, the elastic spring member is compressed, thus generating the elastic force. Here, the position of the locking member may move along the pillar member at the top of the pillar member so that a degree that the elastic spring member is compressed is controlled.

In particular, in the apparatus for measuring the strength of concrete according to the present invention, the controller may be configured to calculate a function for a time of the detection signal of the ultrasonic reception probe, calculate a wavelet transform function indicative of a wavelet transform signal for the detection signal of the ultrasonic reception probe by performing a wavelet transform on the detection signal of the ultrasonic reception unit, calculate a time t corresponding to a maximum value of the wavelet transform function, calculate the propagation velocity $V_{Surface\ wave}$ of the surface wave included in the ultrasonic waves applied to the concrete through the ultrasonic transmission probe by dividing a distance d between the ultrasonic transmission probe and the ultrasonic reception probe by the calculated time t, and measure the strength of the concrete by reading the strength of the concrete corresponding to the calculated propagation velocity $V_{Surface\ wave}$ of the surface wave from a database in which a relationship between the propagation velocity of the surface wave and the strength of the concrete has been constructed.

Furthermore, the present invention provides a slip form construction method of measuring the strength of concrete precisely based on the velocity of ultrasonic waves that varies depending on the degree of the curing of the concrete and determining the slip-up speed of the concrete form by casting the concrete while raising the slip form, installing the apparatus for measuring the strength of concrete in the slip form, and measuring the strength of the concrete by radiating the ultrasonic waves to the concrete cast in the slip form.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Some exemplary embodiments of the present invention are described with reference to the accompanying drawings. The embodiments of the present invention are described with reference to the illustrated drawings, but are only illustrative, and the technical spirit, essential constructions, and actions of the present invention are not restricted by the embodiments.

Figure 1:
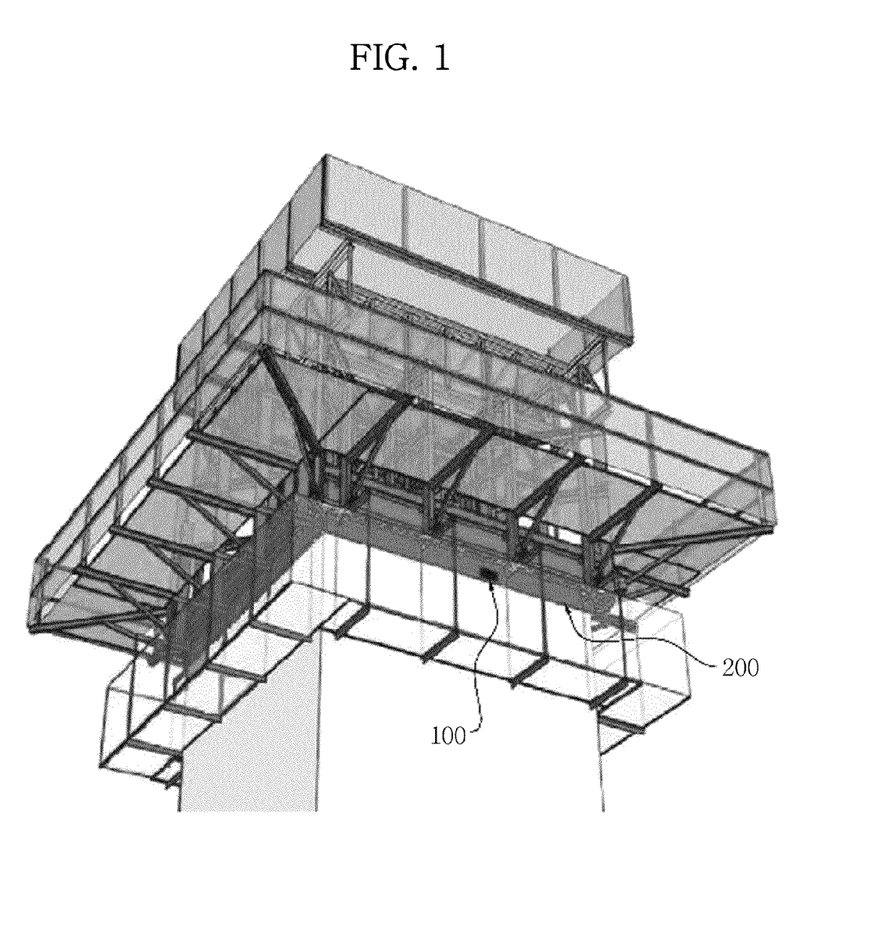
FIG. 1 shows a shape in which the pylon of a bridge, that is, an example of a concrete column member, is constructed using a slip form method and is a schematic perspective view showing the state in which a surface wave velocity measurement device in accordance with the present invention is installed in a slip form.
Figure 2:
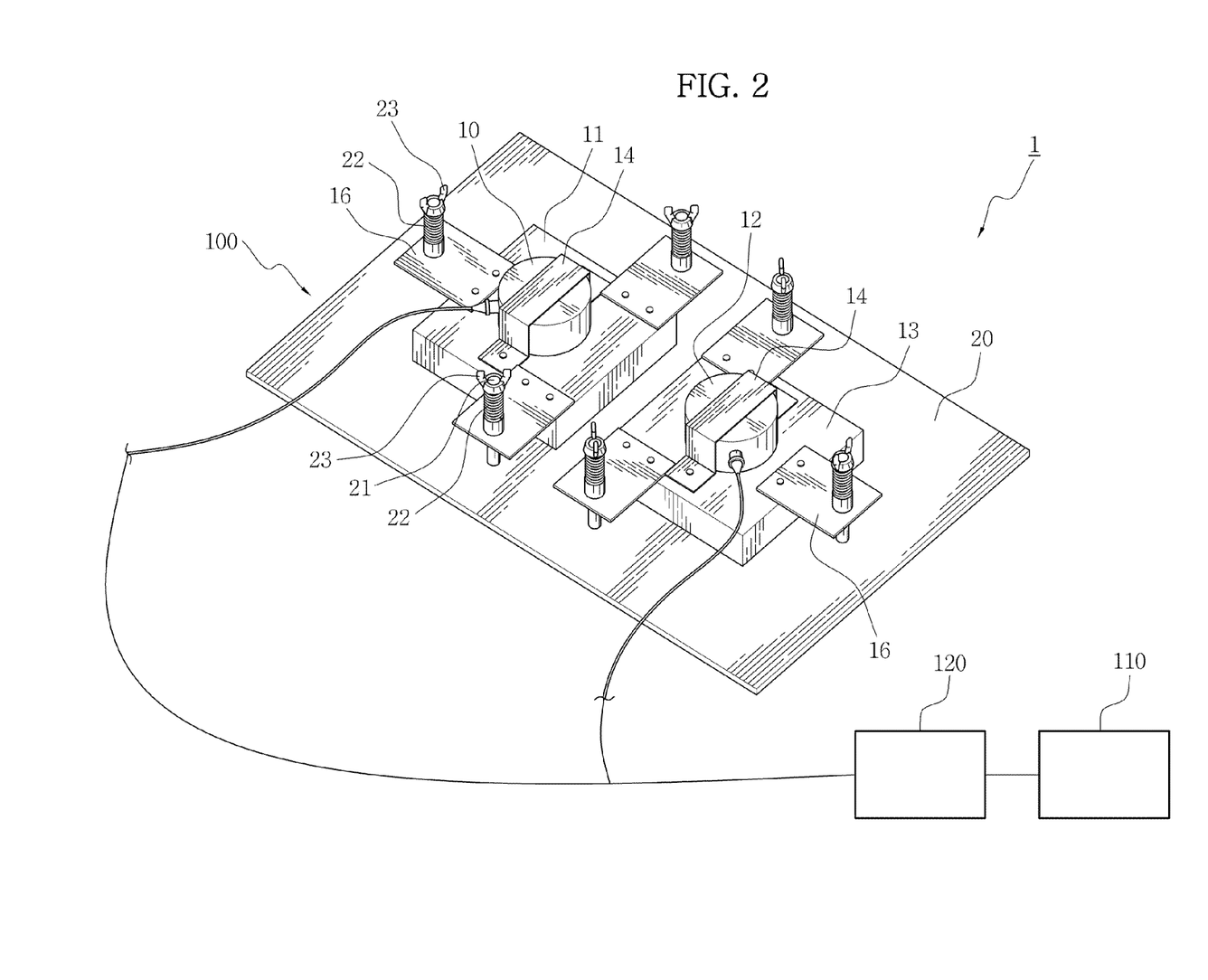
FIG. 2 is a schematic perspective view of the surface wave velocity measurement device in accordance with an embodiment of the present invention.
Figure 3:
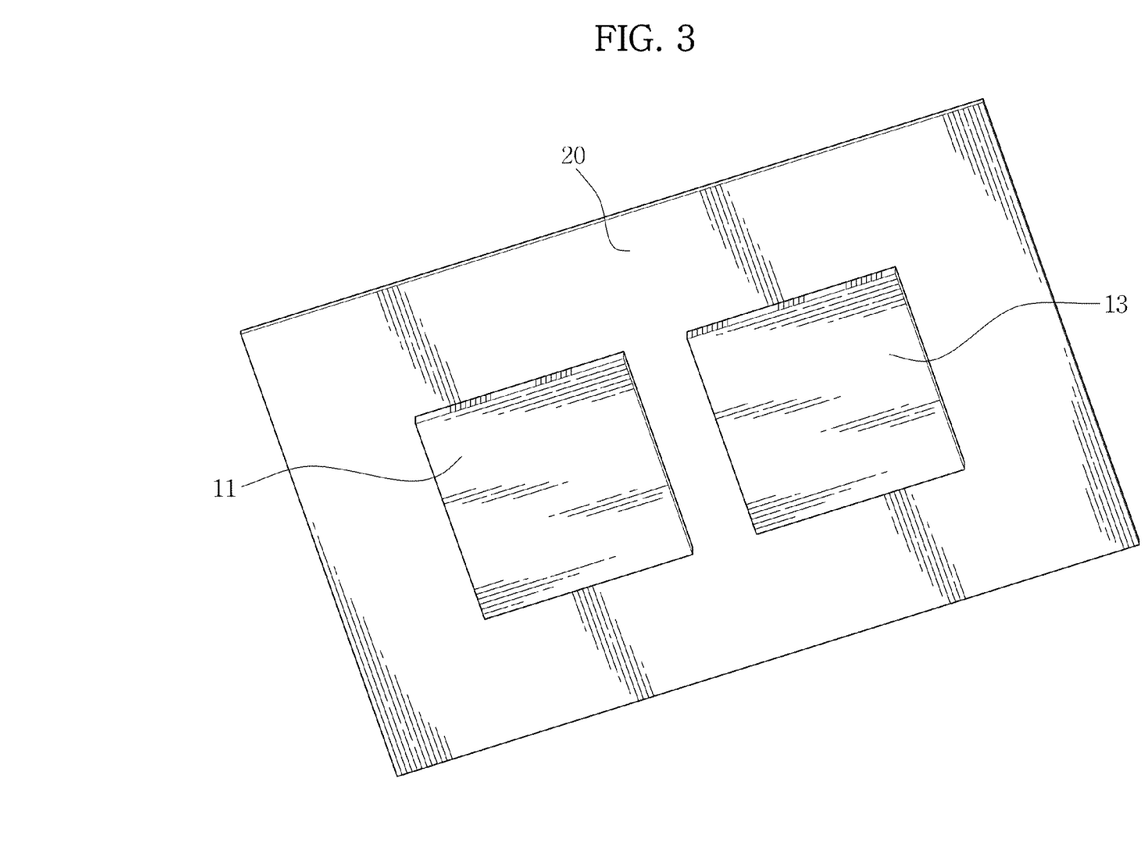
FIG. 3 is a schematic perspective view showing the bottom of the surface wave velocity measurement device shown in FIG. 2.
Figure 4:
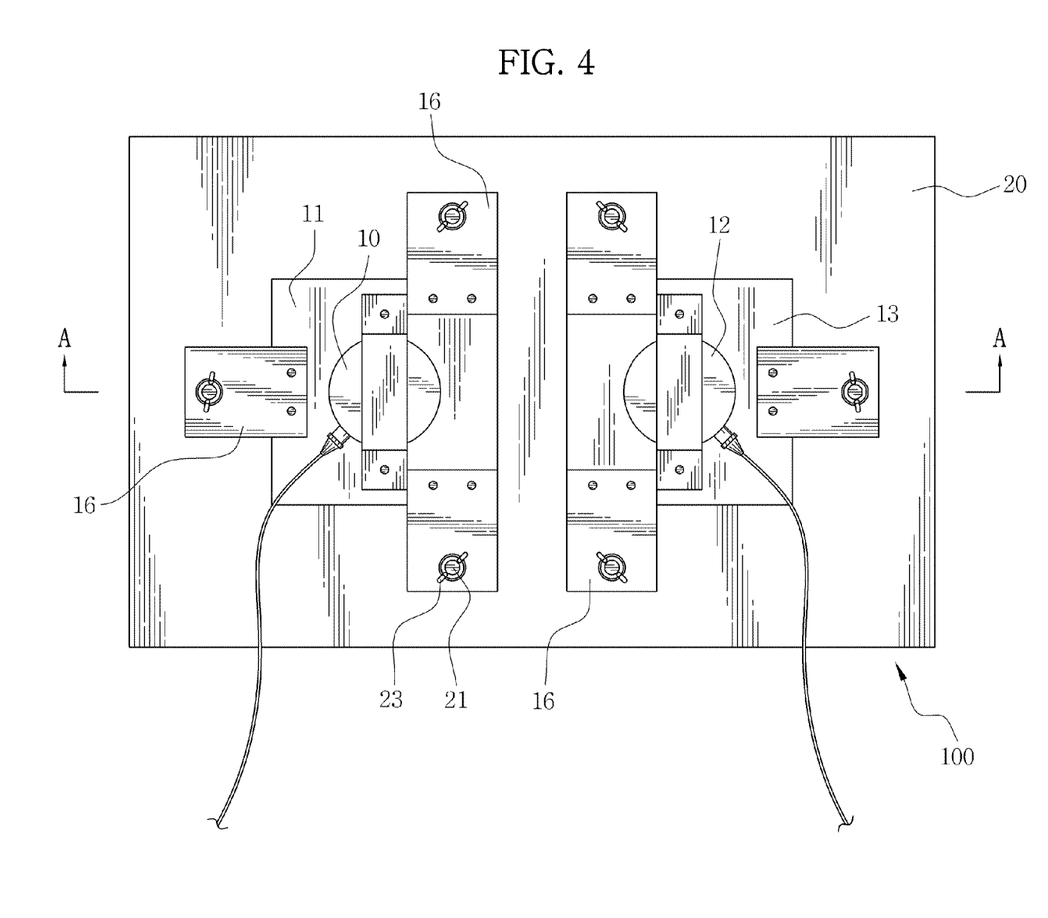
FIG. 4 is a schematic plan view of the surface wave velocity measurement device in accordance with the present invention shown in FIG. 2.
Figure 5:
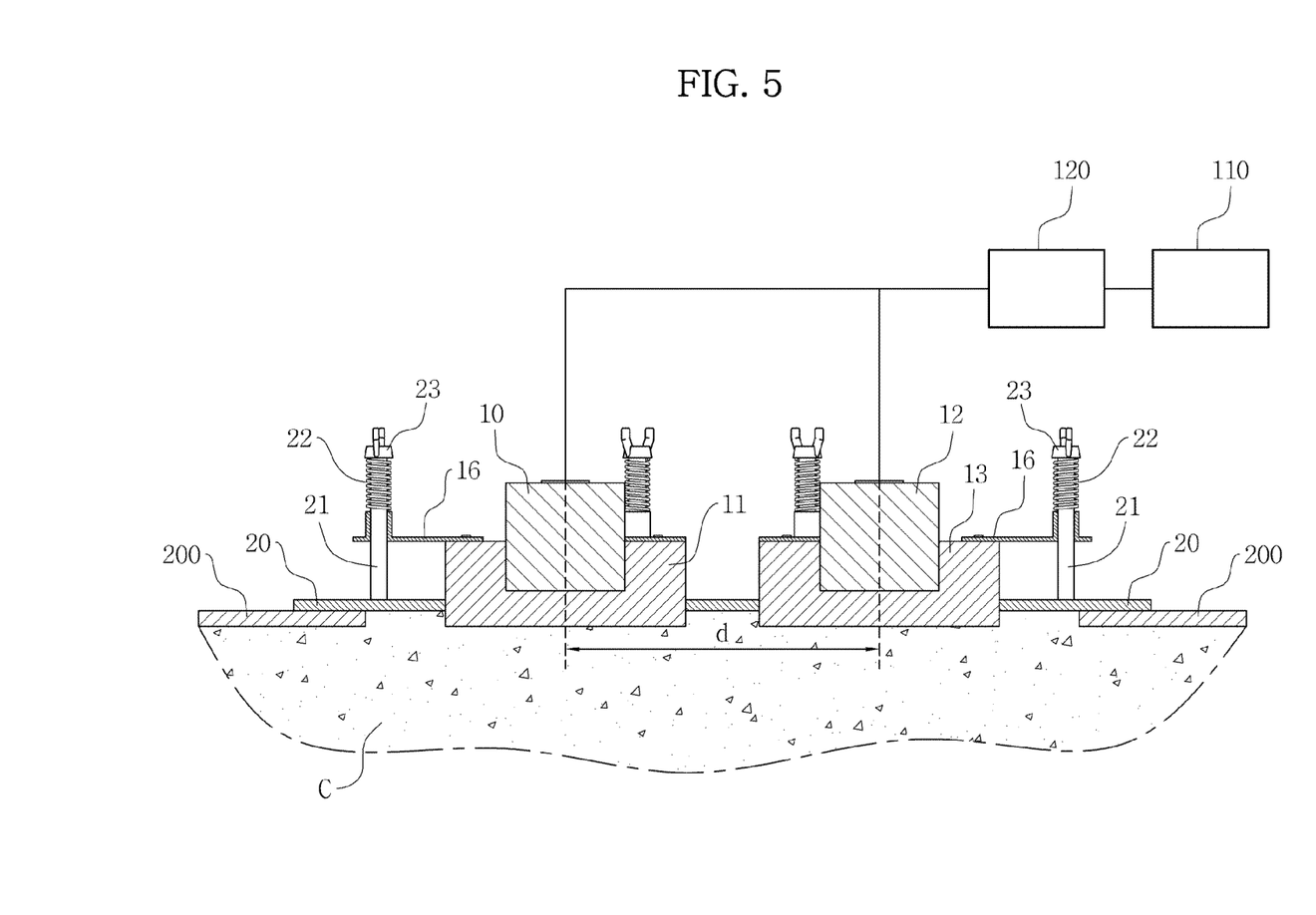
FIG. 5 is a cross-sectional view taken along line A-A of FIG. 4 and is a schematic cross-sectional view showing the state in which the surface wave velocity measurement device in accordance with the present invention is closely adhered to concrete.

FIG. 1 shows a shape in which the pylon of a bridge, that is, an example of a concrete column member, is constructed using a slip form method, and it is a schematic perspective view showing the state in which an surface wave velocity measurement device 100, that is, a member that forms an apparatus 1 for measuring the strength of concrete, in accordance with the present invention is installed in a slip form 200. FIG. 2 is a schematic perspective view of the surface wave velocity measurement device 100 in accordance with an embodiment of the present invention, and FIG. 3 is a schematic perspective view showing the bottom of the surface wave velocity measurement device 100 shown in FIG. 2. FIG. 4 is a schematic plan view of the surface wave velocity measurement device 100 in accordance with the present invention shown in FIG. 2, and FIG. 5 is a cross-sectional view taken along line A-A of FIG. 4 and is a schematic cross-sectional view showing the state in which the surface wave velocity measurement device 100 in accordance with the present invention is closely adhered to concrete C. For reference, in FIGS. 2 and 5, a controller 110 that forms an apparatus 1 for measuring the strength of concrete and a signal converter 120 in accordance with the present invention are simplified into a block and shown.

As shown, the apparatus 1 for measuring the strength of concrete in accordance with the present invention includes the surface wave velocity measurement device 100 installed in concrete and configured to generate ultrasonic waves to the concrete and to measure the propagation velocity of the ultrasonic waves propagating along the concrete and the controller 110 configured to calculate the strength of concrete based on a signal measured by the surface wave velocity measurement device 100. The apparatus 1 for measuring the strength of concrete may further include the signal converter 120 configured to convert the measured signal of the surface wave velocity measurement device 100 into a signal state that can be processed and send the processed signal to the controller 110.

First, the construction of the surface wave velocity measurement device 100 is described below. The surface wave velocity measurement device 100 includes an ultrasonic transmission probe 10 configured to generate ultrasonic waves within concrete, a first contact plate 11 configured to have the ultrasonic transmission probe 10 installed therein, closely adhered to a surface of concrete C, and configured to transfer the ultrasonic waves generated from the ultrasonic transmission probe 10 to the concrete C, an ultrasonic reception probe 12 configured to detect ultrasonic waves that propagate through the concrete, a second contact plate 13 configured to have the ultrasonic reception probe 12 installed therein, closely adhered to the surface of the concrete, and configured to transfer the ultrasonic waves from the concrete to the ultrasonic reception probe 12, and a frame 20 configured to have the first contact plate 11 and the second contact plate 13 combined therewith and assembled into the slip form 200.

Particularly, the frame 20 is a member that is assembled into and installed in the slip form 200 and also a member where the ultrasonic transmission probe 10 and the ultrasonic reception probe 12 are installed. In the embodiment shown in the figure, two openings spaced apart from each other are formed in the frame 20, and the first contact plate 11 and the second contact plate 13 are inserted into the respective openings. As shown in FIG. 3, the bottom of the first contact plate 11 and the bottom of the second contact plate 13 are placed in the downward direction of the frame 20.

The ultrasonic transmission probe 10 is installed in the first contact plate 11. In the embodiment shown in the figure, a groove is concavely formed from a top surface of the first contact plate 11, and the ultrasonic transmission probe 10 is inserted into the concave groove. The ultrasonic reception probe 12 is installed in the second contact plate 13. In the embodiment shown in the figure, like in the first contact plate 11, a groove is concavely formed from a top surface of the second contact plate 13, and the ultrasonic reception probe 12 is inserted into the groove. As described above, the ultrasonic transmission probe 10 and the ultrasonic reception probe 12 are disposed in the first contact plate 11 and the second contact plate 13, respectively, and the bottom of the first contact plate 11 and the bottom of the second contact plate 13 come in contact with the surface of the concrete C. Thus, the ultrasonic transmission probe 10 and the ultrasonic reception probe 12 can be prevented from being damaged or abraded owing to contact with the concrete C. The first contact plate 11 and the second contact plate 13 may be made of synthetic resin, such as acryl. If the first contact plate 11 and the second contact plate 13 are made of acryl, there is an advantage in that the transfer of a signal and the detection of a signal are very excellent. Furthermore, if the first contact plate 11 and the second contact plate 13 are made of synthetic resin, such as acryl, the costs of production is low and thus the first contact plate 11 and the second contact plate 13 can be easily replaced if they are damaged or abraded.

The first contact plate 11 and the second contact plate 13 are disposed with them being spaced apart from each other at a specific interval in the frame 20, and thus the ultrasonic transmission probe 10 and the ultrasonic reception probe 12 are disposed with them being spaced apart from each other at a specific interval d. In FIG. 2, reference numeral 14 is coupling pieces 14 for fixing and maintaining the ultrasonic transmission probe 10 and the ultrasonic reception probe 12, respectively, so that they do not exit from the grooves of the first contact plate 11 and the second contact plate 13. The ultrasonic transmission probe 10 for generating ultrasonic waves is known in the art, and thus the known ultrasonic transmission probe 10 is used in the present invention. The ultrasonic reception probe 12 for detecting and receiving ultrasonic waves is also known in the art, and thus the known ultrasonic reception probe 12 is used in the present invention.

As will be described later, when combining the surface wave velocity measurement device 100 of the present invention with the slip form 200 and installing it on the surface of the concrete, it is very important to have the bottom of the first contact plate 11 and the bottom of the second contact plate 13 closely adhered to the surface of the concrete. To this end, the surface wave velocity measurement device 100 of the present invention may be configured to apply pressure to the first contact plate 11 and the second contact plate 13 in their downward directions. That is, the bottom of the first contact plate 11 may be more protruded than the bottom of the frame 20, wherein an elastic spring member extended or compressed when the first contact plate 11 retreats in the upward direction of the frame 20 and configured to apply elastic force to the first contact plate 11 toward the bottom of the first contact plate 11 is disposed between the first contact plate 11 and the frame 20. The same principle applies to the second contact plate 13.

FIGS. 2 and 5 show detailed constructions for applying pressure to the first contact plate 11 and the second contact plate 13 in their downward directions using the spring member. In the embodiment shown in the figure, a pillar member 21 is disposed near the first contact plate 11 on the top surface of the frame 20, and a coupling piece 16 is included in the first contact plate 11. After the pillar member 21 penetrates the coupling piece 16, a coil-shaped elastic spring member 22 is disposed over the coupling piece 16 in the pillar member 21. A locking member 23 is included at the top of the elastic spring member 22. A plurality of, for example, two or more pillar members 21 are included near the first contact plate 11.

In this construction, when the bottom of the first contact plate 11 more protruded than the bottom of the frame 20 comes in contact with the surface of the concrete C and thus retreats, that is, when the first contact plate 11 moves in the upward direction of the frame 20, the coupling piece 16 rises toward the top of the pillar member 21 in the state in which one side of the coupling piece 16 is inserted into the pillar member 21. Since the spring member 22 is disposed between the top of the coupling piece 16 and the locking member 23 at the end of the pillar member 21, the spring member 22 is compressed when the coupling piece 16 rises, so that pressure is applied to the coupling piece 16. That is, pressure that pushes the coupling piece 16 toward the top of the frame 20 is applied to the top surface of the coupling piece 16 by the spring member 22. The application of pressure to the top surface of the coupling piece 16 as described above results in the application of the pressure from the top surface of the first contact plate 11 to a downward direction thereof. This pressure has an effect in which the first contact plate 11 is further closely adhered to the surface of the concrete C. The locking member 23 may be combined at the top of the pillar member 21 so that the position of the locking member 23 moves along the pillar member 21. In this case, if the locking member 23 is moved toward the lower side of the pillar member 21 and thus compresses the spring member 22, additional pressure is further applied to the coupling piece 16 of the first contact plate 11, so that the first contact plate 11 is further closely adhered to the surface of the concrete C. The position of the locking member 23 may be changed at the top of the pillar member 21 by forming a screw unit at the top of the pillar member 21 and screwing the locking member 23. In accordance with this construction, the pressure applied to the coupling piece 16 can be easily controlled because the position of the locking member 23 can be conveniently changed.

As described above, in the present invention, the coupling piece 16 is installed in the first contact plate 11, and the elastic spring member 22 is disposed between members (i.e., the pillar member 21 and the locking member 23), fixed to the frame 20, and the top surface of the coupling piece 16. Thus, when the first contact plate 11 retreats in its top direction and thus the coupling piece 16 moves, elastic force is generated from the elastic spring member 22, and the elastic force pushes the first contact plate 11 in its downward direction. This pressure is applied to the first contact plate 11. Accordingly, there is an advantage in that the first contact plate 11 is always closely adhered to the surface of the concrete C.

Although the first contact plate 11 is illustrated as an example, the second contact plate 13 is constructed so that pressure is applied to the second contact plate 13 like the first contact plate 11.

A method of constructing a concrete column member by measuring the strength of concrete using the apparatus 1 for measuring the strength of concrete including the surface wave velocity measurement device 100 in accordance with the present invention and raising a slip form based on the measured strength is described below.

In the present invention, the surface wave velocity measurement device 100 is installed in the opened parts of the slip form 200. Particularly, opened parts are formed in the slip form 200, and the edge of the frame 20 is combined with the slip form 200 so that the first contact plate 11 and the second contact plate 13 are placed in the opened parts of the slip form 200. A magnet may be installed at the edge of the frame 20 so that the edge of the frame 20 is attached to the slip form 200.

When the surface wave velocity measurement device 100 is combined with the opened parts of the slip form 200, the bottom of the first contact plate 11 and the bottom of the second contact plate 13 are closely adhered to the surface of the concrete C through the opened parts of the slip form 200.

In the state in which the first contact plate 11 and the second contact plate 13 are closely adhered to the surface of the concrete C, the ultrasonic transmission probe 10 generates ultrasonic waves and the generated ultrasonic waves are applied to the concrete C via the first contact plate 11 at step S1. Here, the ultrasonic waves applied to the concrete C include a surface wave that flows through the surface of the concrete C. The ultrasonic reception probe 12 detects an ultrasonic wave signal that is generated in the concrete C by the ultrasonic transmission probe 10 and propagated at step S2.

The controller 110 calculates the strength of the concrete from the detected ultrasonic wave signal. The signal converter 120 performs a signal conversion task so that the signal detected by the ultrasonic reception probe 12 is converted into a digital signal and the digital signal is transferred to the controller 110 at step S3. The signal converter 120 may include an Analog/Digital (A/D) converter for converting an analog signal into a digital signal. The A/D converter converts the signal, detected by the ultrasonic reception probe 12, into the digital signal and transfers the digital signal to the controller 110.

Figure 6:
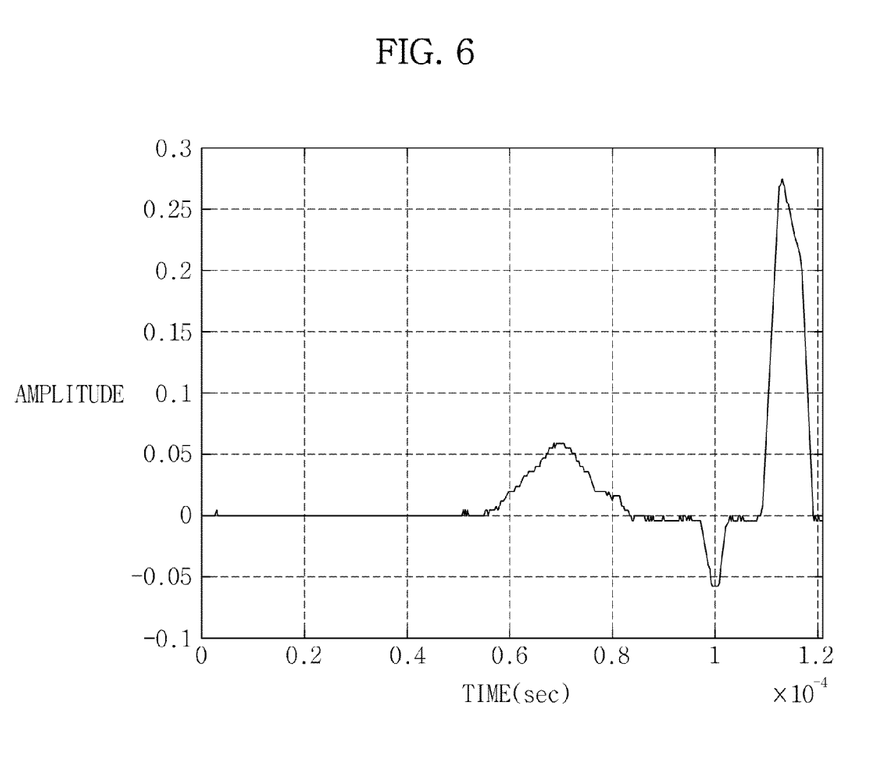
FIG. 6 is a graph showing an exemplary signal detected by an ultrasonic reception probe that is included in the surface wave velocity measurement device in accordance with the present invention.

FIG. 6 is a graph showing an exemplary signal detected by the ultrasonic reception probe 12. In FIG. 6, a vertical axis is amplitude, and a horizontal axis is the time (sec). Although the signal converter 120 converts the analog signal, detected by the ultrasonic reception probe 12, into the digital signal, the signal detected by the ultrasonic reception probe 12 includes not only a surface wave, but also other various forms of ultrasonic waves, such as a compression wave and a shear wave. Accordingly, it is difficult to distinguish only the surface wave from the detection signal converted into the digital signal through the signal converter 120. In order to solve this problem, in the present invention, the detection signal of the ultrasonic reception probe 12 is subjected to a wavelet transform at step S4.

Particularly, the controller 110 performs a wavelet transform on the detection signal of the ultrasonic reception probe 12 that has been converted into the digital signal in accordance with Equations 1 and 2 below.

$$W(b,a) = \frac{1}{\sqrt{a}} \int_{-\infty}^{+\infty} f(t) \psi\left(\frac{t-b}{a}\right) dt \qquad \text{Equation 1}$$

$$\psi(t) = \exp\left(-\frac{t^2}{2}\right) \cos(5t) \qquad \text{Equation 2}$$

In Equation 1 and Equation 2, f(t) is a function for the detection signal of the ultrasonic reception probe 12. When the signal converter 120 converts the detection signal of the ultrasonic reception probe 12 into the digital signal, the function f(t) having a graph of the time in the horizontal axis—the amplitude in the vertical axis for the detection signal of the ultrasonic reception probe 12 can be obtained.

In Equation 1 and Equation 2, W(b,a) is a wavelet transform signal function that is obtained by performing a wavelet transform on the function f(t) for the time in the horizontal axis—the amplitude in the vertical axis, that is, a function indicative of the wavelet transform signal for the detection signal of the ultrasonic reception probe 12.

When the wavelet transform is performed on the function f(t) for the detection signal of the ultrasonic reception probe 12 in accordance with Equation 1 and Equation 2 as described above, the wavelet transform signal W(b,a) for the detection signal of the ultrasonic reception probe 12 can be obtained.

In Equation 1 and Equation 2, 'a' is a compression coefficient for determining the size of a wavelet, that is, a scale, and is a coefficient that is randomly determined by determining a scale desired by a user. In Equation 1 and Equation 2, 'b' is a transition coefficient that is related to a movement in the time axis, and it corresponds to a value of the digital signal in the time axis that has been converted by the A/D converter 14.

Figure 7:
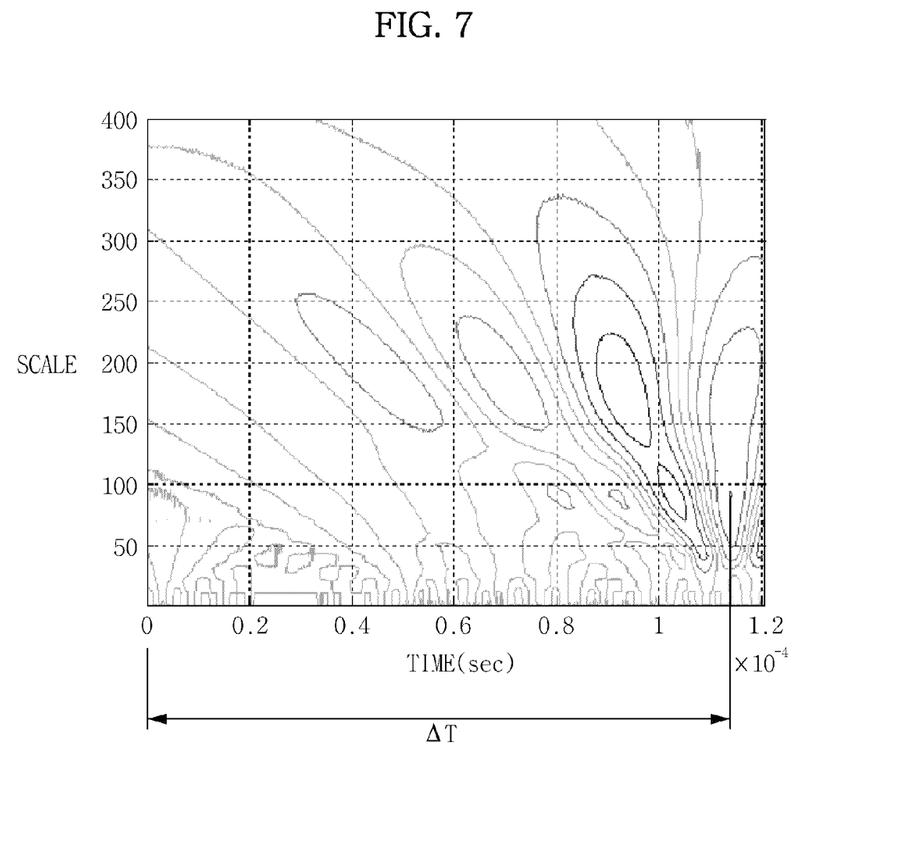
FIG. 7 is a graph showing the state in which the signal shown in FIG. 6 is subjected to a wavelet transform.

If this wavelet transform process is performed, only a detection signal for the surface wave can be extracted from the detection signal of the ultrasonic reception probe 12. FIG. 7 is a graph showing the state in which the signal illustrated in the graph of FIG. 6 is subjected to a wavelet transform. In FIG. 7, the horizontal axis is the time (sec), the vertical axis is a scale, and a contour is shown in graph.

In the present invention, when the wavelet transform signal is generated from the detection signal of the ultrasonic reception probe 12 through the wavelet transform process, the time corresponding to a maximum value of the wavelet transform signal for the ultrasonic reception probe 12 is calculated at step S5. That is, the wavelet transform function W(b,a) is calculated by performing the wavelet transform process on the detection signal of the ultrasonic reception probe 12, and the time t corresponding to a maximum value of the wavelet transform function is then calculated. For example, in the graph of the wavelet transform signal, time t ($\Delta T$ in FIG. 7 assuming that a measurement start time is 0) can be calculated by reading a time value in the horizontal axis at which a signal value becomes a maximum.

After calculating the value of the time t, the velocity of the surface wave is calculated by dividing the distance d between the ultrasonic transmission probe 10 and the ultrasonic reception probe 12 by the value of the time t at step S6. That is, the propagation velocity of the surface wave, that is, the propagation velocity $V_{Surface\ wave}$ of the surface wave, from among the ultrasonic waves applied to the concrete C by the ultrasonic transmission probe 10 is calculated by Equation 3 below.

$$V_{surface\ wave} = \frac{d}{t} \qquad \text{Equation 3}$$

A relationship between the propagation velocity $V_{Surface\ wave}$ of the surface wave and the strength of concrete has already been databased by the existing researches. Thus, the strength of the concrete C to be measured can be obtained by reading the strength of the concrete C from the database based on the obtained propagation velocity $V_{Surface\ wave}$ of the surface wave at step S7.

Figure 8:
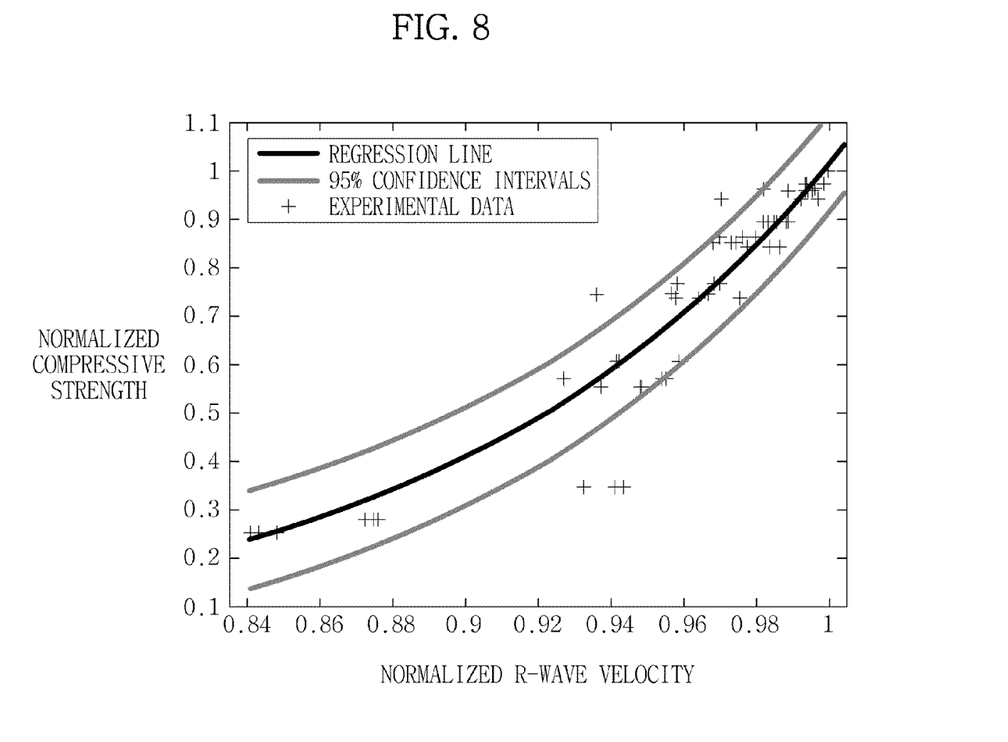
FIG. 8 is a graph showing a relationship between the velocity of a surface wave and the strength of concrete which was induced by the existing researches.

FIG. 8 is a graph showing a relationship between the velocity of the surface wave and the strength of the concrete which was induced by the existing researches. In FIG. 8, the vertical axis is normalized compressive strength, the horizontal axis is normalized surface wave (R-wave) velocity, a +shaped pattern is experimental data, a thick line in the center is a regression line based on the experimental data, and two lines on both sides of the thick line in the center indicate 95% confidence intervals.

That is, if the propagation velocity $V_{Surface\ wave}$ of the surface wave applied to the concrete C by the ultrasonic transmission probe 10 is calculated by the method of the present invention, a result of the calculation is set as a value in the horizontal axis in a relationship between the velocity of an surface wave and the strength of concrete which has already been known as in, for example, FIG. 8, and the strength of the concrete C can be obtained by reading a value in the vertical axis.

After the strength of the concrete C cast in the slip form is calculated based on the propagation velocity of the surface wave through the above process, whether the strength of the concrete necessary to raise the slip form has been reached or not is determined, and whether to raise the slip form or not is determined based on a result of the determination at step S8.

Figure 9:
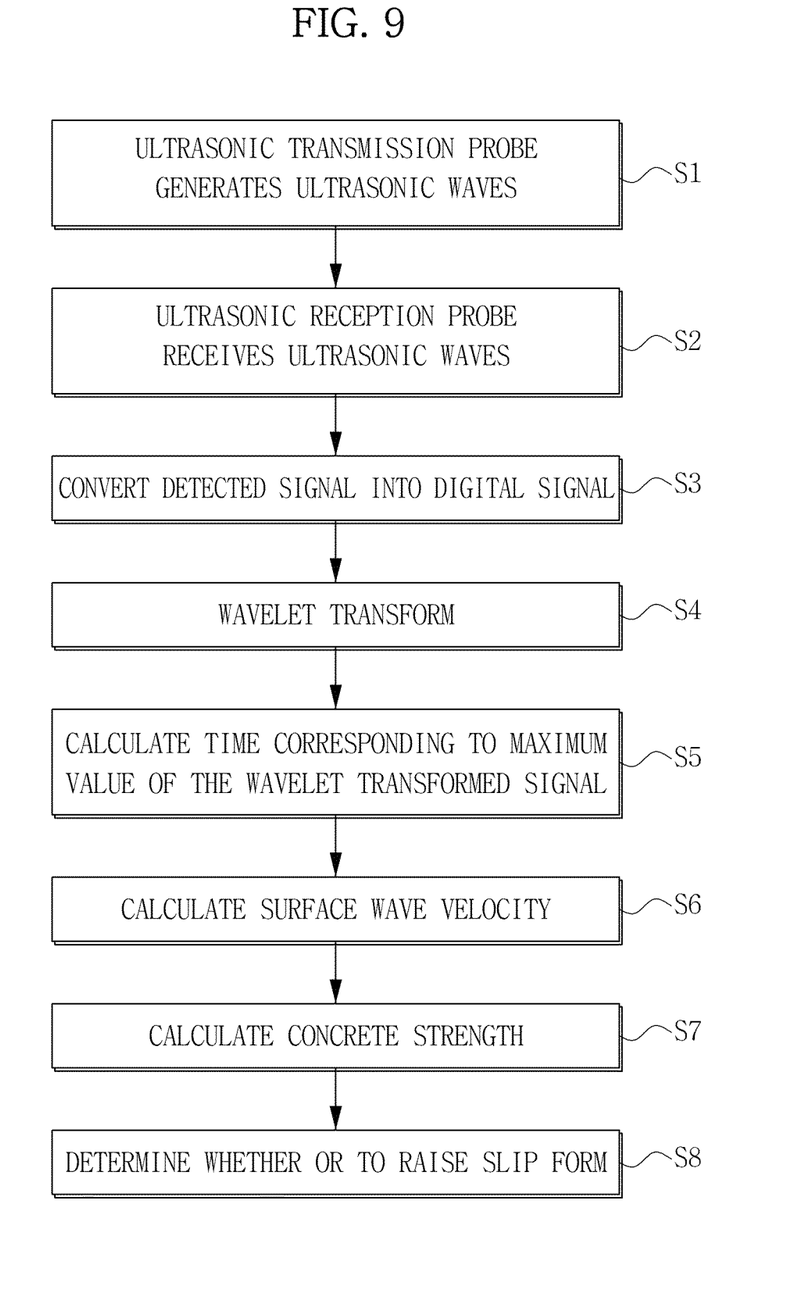
FIG. 9 is a flowchart illustrating a method of raising a slip form in accordance with the present invention.

FIG. 9 is a flowchart illustrating the method of raising a slip form in accordance with the present invention. As shown in FIG. 9, the process of the ultrasonic transmission probe 10 generating the ultrasonic waves (step S1), the ultrasonic reception probe 12 detecting the ultrasonic waves (step S2), converting the detected signal into the digital signal (step S3), performing the wavelet transform (step S4), the ultrasonic transmission probe 10 calculating the propagation velocity $V_{Surface\ wave}$ of the surface wave which is included in the ultrasonic waves generated from the concrete C (steps S5 and S6), and reading and calculating the strength of the concrete based on the propagation velocity $V_{Surface\ wave}$ of the surface wave (step S7) is repeated. Whether to raise the slip form or not is determined by determining whether the read strength of the concrete has reached strength suitable for raising the slip form or not (step S8). That is, if the strength of the concrete read according to the present invention is predetermined strength which is suitable for raising the slip form or more, the slip form is raised.

As described above, the present invention is advantageous in that a data analysis process is reduced because a wavelet transform task is performed on only the one ultrasonic reception probe 12 and more accurate measurement is possible because noise is less likely to be included in a measured signal.

In accordance with the present invention, in constructing a concrete column member, such as a concrete pylon or a concrete pier, by casting concrete stepwise according to a rise of a slip form, the concrete column member can be constructed stably and rapidly by checking the setting time of the concrete and determining the slip-up time of the slip form using a method of measuring the strength of the concrete cast in the slip form quantitatively, precisely, and in such a way not to damage the concrete.

In particular, in the present invention, the strength of concrete is measured using the surface wave velocity measurement device having a simple structure. Accordingly, there are advantages in that accuracy can be increased when measuring the strength of concrete, the time taken to measure the strength of concrete can be reduced, construction efficiency can be improved and costs can be reduced.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for measuring a strength of concrete, comprising:
    an surface wave velocity measurement device installed in concrete and configured to generate ultrasonic waves to the concrete and to detect ultrasonic waves propagated along the concrete; and
    a controller configured to calculate a propagation velocity of a surface wave included in the ultrasonic waves by converting a signal measured by the surface wave velocity measurement device and calculate the strength of the concrete based on a result of the calculation,
    wherein the surface wave velocity measurement device comprises:
    an ultrasonic transmission probe configured to generate the ultrasonic waves within the concrete,
    a first contact plate configured to have the ultrasonic transmission probe installed therein, closely adhered to a surface of the concrete, and configured to transfer the ultrasonic waves of the ultrasonic transmission probe to the concrete, an ultrasonic reception probe configured to detect the ultrasonic waves propagated through the concrete, a second contact plate configured to have the ultrasonic reception probe installed therein, closely adhered to the surface of the concrete, and configured to transfer the ultrasonic waves from the concrete to the ultrasonic reception probe, and a frame configured to have two openings formed therein at an interval, configured to have the first contact plate and the second contact plate inserted into and combined with the respective openings, and assembled into a slip form.

2. The apparatus as set forth in claim 1, wherein the controller is configured to:

calculate a function f(t) for a time of the detection signal of the ultrasonic reception probe, calculate a wavelet transform function W(b,a) indicative of a wavelet transform signal for the detection signal of the ultrasonic reception probe by performing a wavelet transform on the detection signal of the ultrasonic reception unit based on an equation:

$$W(b, a) = \frac{1}{\sqrt{a}} \int_{-\infty}^{+\infty} f(t)\psi\left(\frac{t-b}{a}\right)dt, \text{ where } \psi(t) = \exp\left(-\frac{t^2}{2}\right)\cos(5t),$$

where 'a' is a compression coefficient for determining a scale of a wavelet and 'b' is a transition coefficient related to a movement in a time axis, calculate a time t corresponding to a maximum value of the wavelet transform function W(b,a), calculate the propagation velocity of the surface wave included in the ultrasonic waves applied to the concrete through the ultrasonic transmission probe by dividing a distance d between the ultrasonic transmission probe and the ultrasonic reception probe by the calculated time t, and measure the strength of the concrete by reading the strength of the concrete corresponding to the calculated propagation velocity of the surface wave from a database in which a relationship between the propagation velocity of the surface wave and the strength of the concrete has been constructed.

3. The apparatus as set forth in claim 1, wherein:

a bottom of the first contact plate and a bottom of the second contact plate are disposed in such a way as to be more protruded than a bottom of the frame;

coupling pieces are installed in the first contact plate and the second contact plate, respectively;

an elastic spring member is disposed between a member fixed to the frame and a top surface of each of the coupling pieces; and when the bottom of each of the first contact plate and the second contact plate protruded further than the bottom of the frame comes in contact with the surface of the concrete and thus retreats in an upward direction of the frame, the coupling piece moves and thus the elastic spring member generates elastic force, and the elastic force of the elastic spring member functions as pressure that pushes each of the first contact plate and the second contact plate in a downward direction thereof.

4. The apparatus as set forth in claim 3, wherein:

the member fixed to the frame comprises a pillar member vertically installed in the frame and a locking member provided at a top of the pillar member;

the pillar member penetrates the coupling piece; and the elastic spring member is included between a top of the coupling piece and the locking member in the pillar member after the pillar member penetrates the coupling piece, and thus when the coupling piece moves, the elastic spring member is compressed, thus generating the elastic force.

5. The apparatus as set forth in claim 4, wherein a position of the locking member moves along the pillar member at the top of the pillar member so that a degree that the elastic spring member is compressed is controlled.

6. A slip form construction method of fabricating a vertical concrete column member by casting concrete while raising a sliding slip form, the slip form construction method comprising the steps of:

measuring a strength of concrete by a process of:

installing an surface wave velocity measurement device, comprising an ultrasonic transmission probe configured to generate the ultrasonic waves within the concrete, a first contact plate configured to have the ultrasonic transmission probe installed therein, closely adhered to a surface of the concrete, and configured to transfer the ultrasonic waves of the ultrasonic transmission probe to the concrete, an ultrasonic reception probe configured to detect the ultrasonic waves propagated through the concrete, a second contact plate configured to have the ultrasonic reception probe installed therein, closely adhered to the surface of the concrete, and configured to transfer the ultrasonic waves from the concrete to the ultrasonic reception probe, and a frame configured to have two openings formed therein at an interval, configured to have the first contact plate and the second contact plate inserted into and combined with the respective openings, and assembled into a slip form, in openings formed in the slip form and then closely adhering a bottom of the first contact plate and a bottom of the second contact plate to the surface of the concrete, generating the ultrasonic waves of an surface wave form in the concrete C casted in the slip form using the ultrasonic transmission probe, detecting the ultrasonic waves of the concrete using the ultrasonic reception probe, converting the detection signal of the ultrasonic reception probe into a digital signal, and calculating a function f(t) for a time of the detection signal of the ultrasonic reception unit, calculating a wavelet transform function W(b,a) indicative of a wavelet transform signal for the detection signal of the ultrasonic reception unit by performing a wavelet transform on the detection signal of the ultrasonic reception unit based on an equation:

$$W(b, a) = \frac{1}{\sqrt{a}} \int_{-\infty}^{+\infty} f(t)\psi\left(\frac{t-b}{a}\right)dt, \text{ where } \psi(t) = \exp\left(-\frac{t^2}{2}\right)\cos(5t),$$

where 'a' is a compression coefficient for determining a scale of a wavelet and 'b' is a transition coefficient related to a movement in a time axis, calculating a time t corresponding to a maximum value of the wavelet transform function W(b,a) and calculating a propagation velocity of the surface wave included in the ultrasonic waves applied to the concrete through the ultrasonic transmission probe by dividing a distance d between the ultrasonic transmission probe and the ultrasonic reception probe by the calculated time t, and measuring a strength of the concrete by reading a strength of the concrete corresponding to the calculated propagation velocity of the surface wave from a database in which a relationship between the propagation velocity of the surface wave and the strength of the concrete has been constructed; and raising the slip form when the measured strength of the concrete becomes predetermined strength which is suitable for raising the slip form or higher.

* * * * *